United States Patent [19]

Urnovitz et al.

[11] Patent Number: 5,516,638

[45] Date of Patent: May 14, 1996

[54] IMMUNOASSAYS FOR THE DETECTION OF ANTIBODIES TO *CHLAMYDIA TRACHOMATISI* IN THE URINE.

[75] Inventors: Howard B. Urnovitz, San Francisco; Toby D. Gottfried, Orinda; David J. Robison, Walnut Creek, all of Calif.

[73] Assignee: Calypte, Inc., Berkeley, Calif.

[21] Appl. No.: 266,274

[22] Filed: Jun. 27, 1994

Related U.S. Application Data

[63] Continuation of Ser. No. 977,755, Nov. 18, 1992, abandoned.

[51] Int. Cl.$^6$ .............. G01N 33/543; G01N 33/569; G01N 33/571
[52] U.S. Cl. .............. 435/7.32; 435/7.36; 435/7.92; 435/7.93; 435/7.94; 435/7.95; 436/518; 436/530; 436/531; 436/534
[58] Field of Search ................ 435/7.32, 7.36, 435/7.92, 7.93, 7.95, 967, 974, 975; 436/518, 530, 531, 534

[56] References Cited

U.S. PATENT DOCUMENTS

| | | | |
|---|---|---|---|
| 4,427,782 | 1/1984 | Caldwell, et al. | 436/542 |
| 4,766,065 | 8/1988 | Mosier et al. | 435/7 |
| 5,085,986 | 2/1992 | Mauck et al. | 435/7.36 |
| 5,122,446 | 6/1992 | Friedman-Kien et al. | 435/5 |

FOREIGN PATENT DOCUMENTS

| | | |
|---|---|---|
| 017460 | 10/1980 | European Pat. Off. |
| 038150 | 10/1981 | European Pat. Off. |
| 233048 | 8/1987 | European Pat. Off. |
| 363106 | 4/1990 | European Pat. Off. |
| 4-34363 | 2/1992 | Japan . |
| 88/07680 | 10/1988 | WIPO . |
| 90/00061 | 1/1990 | WIPO . |

OTHER PUBLICATIONS

Pudakkainen et al., "Chlamydial Pneumonitis and Its Serodiagnosis in Infants", J. Infect. Dis., 149(4):598–604 (Apr. 1984).

Paul et al. "Evaluation of Three *Chlamydia trachomatis* Immunoassays with an unbiased, Noninvasive Clinical Sample", J. Clin. Microbiol., 28(2):220–222 (Feb. 1990).

Morse et al, "Sexually Transmitted Diseases", pp. 863–868 in Manual of Clinical Microbiology. 4th Ed. (1985).

Dorland's Illustrated Medical Dictionary, p. 822, W. B. Saunders Company (1985).

Caldwell, H. D., et al., "Purification and Partial Characterization of the Major Outer Membrane Protein of *Chlamydia trachomatis*", Infection and Immunity, vol. 31, No. 3, pp. 1161–1176, Mar. 1981.

Primary Examiner—Toni R. Scheiner
Assistant Examiner—Patricia A. Duffy
Attorney, Agent, or Firm—Townsend and Townsend and Crew

[57] ABSTRACT

The present invention provides methods for detecting the presence of antibodies to a microorganism (e.g., *Chlamydia trachomatis*) associated with a sexually transmitted disease in a biological sample, preferably urine. The methods of the invention comprise contacting the sample with an antigen from the microorganism and detecting the formation of an antigen-antibody complex.

20 Claims, 2 Drawing Sheets

IMMUNOASSAYS FOR THE DETECTION OF ANTIBODIES TO *CHLAMYDIA TRACHOMATISI* IN THE URINE.

This is a continuation of application Ser. No. 07/977,755, filed Nov. 18, 1992, now abandoned.

BACKGROUND OF THE INVENTION

The present invention relates to diagnostic kits and methods for the determination of antibodies in biological sample, typically urine. More particularly, it relates to methods and kits for detecting antibodies to microorganisms associated with sexually transmitted diseases.

Sexually transmitted diseases (STDs) include traditional venereal diseases such as syphilis, gonorrhea, chancroid, lymphogranuloma venereum, and granuloma inguinale. The term also encompasses a growing number of other diseases caused by human immunodeficiency viruses (HIV-1 and -2), hepatitis viruses, herpes simplex virus, Type II (HSV-2), and other viruses which have been reported to be sexually transmitted.

Most STDs do not exist as an isolated problem and multiple infections by a number of pathogens are common. The presence of an STD typically indicates high risk sexual behavior that is often associated with the risk of other more serious infections. The increasing importance of potentially incurable viral STDs (e.g. HIV infection) makes the early detection of any STD more crucial to reduce the transmission of these diseases. STDs are typically propagated in core populations with high levels of sexual activity and frequent changes of sexual partners.

In order to control the spread of these diseases, screening tests for gonorrhea, chlamydial infection, syphilis, and HIV infection must be inexpensive, widely available and safe. Most current detection methods rely on serological tests for the presence of antigens or antibodies to the particular pathogen. These assays rely on invasive procedures to obtain blood or serum from a patient suspected of having the disease. These procedures require relatively expensive equipment, such as sterile needles, syringes, skin cleanser and dressing, and in some cases may be hazardous to the health care personnel involved in collecting and analyzing the samples. Thus, there is an urgent need for non-invasive, relatively inexpensive tests for the presence of pathogens associated with STDs.

SUMMARY OF THE INVENTION

The present invention provides methods for detecting the presence of antibodies to a microorganism associated with a sexually transmitted disease in a biological sample, preferably urine. The methods comprise contacting the sample with an antigen from the microorganism and detecting the formation of an antigen-antibody complex.

The method can be used to detect, for example, antibodies to *Chlamydia trachomatis*. In this case, a preferred antigen is a chlamydial surface protein, such as the major outer membrane protein (MOMP).

In one embodiment, the methods comprise the step of binding the antigen to the solid surface, either covalently or noncovalently. The antigen-antibody complex is preferably detected using a labeled anti-human antibody.

In other embodiments, the antibodies in the sample are bound to the solid surface. In these methods, the antigen is preferably labeled and the antigen-antibody complex is detected by measuring the label on the solid surface.

In those methods requiring a label, the label is typically a detectable enzyme, such as alkaline phosphatase. Alternatively, a radiolabel can be used. The methods need not use labelled components and the antigen-antibody complex can be detected by presence of agglutination of the complex.

Finally, the present invention also provides kits for detecting the presence of antibodies to a microorganism associated with a sexually transmitted disease in urine. The kits comprise an antigen capable of forming an immune complex with the antibody, a labeling system and a buffer solution for the preparation of the urine sample.

DESCRIPTION OF THE PREFERRED EMBODIMENT

Figure 1:
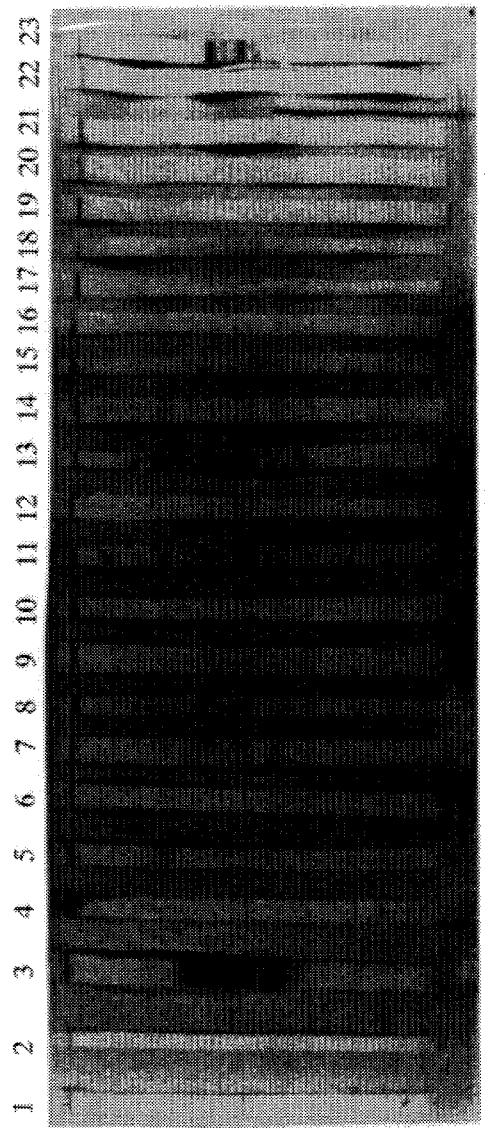
FIG. 1 shows immunoblots demonstrating the presence of *C. trachomatis* in urine samples.

The present invention relates to the detection of antibodies to microorganisms associated with STDs. As used herein "microorganisms associated with STDs" are nonviral, typically single-celled, pathogens, such as bacteria, mycoplasmas, spirochaetes, protozoans, fungi, and the like.

A number of microorganisms have been associated with STDs and can be assayed using the methods of the present invention. Examples include, *Neisseria gonorrhoeae*, *Chlamydia trachomatis*, *Haemophilus ducreyi*, *Calymmatobacterium granulomatis*, *Ureaplasma urealyticum*, *Mycoplasma spp.* (e.g. *M. hominis*, *M. genitalium*, *M. pirum*, and *M. fermentans*), *Toxoplasma gondii*, *Actinomyces israelii*, *Campylobacter spp.*, *Treponema pallidum*, *Trichomonas vaginalis*, and *Candida albicans*.

The ability of the methods of the present invention to detect microorganisms associated with STDs is illustrated by the detection of *Chlamydia trachomatis*, a common pathogen in nongonococcal urethritis (NGU). Members of the genus have a wide host range, including humans. In the U.S., approximately 4 million cases of *C. trachomatis* infection are reported annually. The manifestations of infection include pelvic inflammatory disease (PID), infertility in women, ophthalmic infections, and pulmonary infections.

*C. trachomatis* is an obligate intracellular bacterium with a complex life cycle. The infectious entity is known as an elementary body and is the form responsible for spread within and among hosts. The non-infectious form is called a reticulate body. As the microbe matures, the reticulate body reverts to an infectious elementary body. In women, the elementary bodies are thought to infect urethral epithelial cells. It has been estimated that up to 50% of the cases of PID can exist as "silent carrier" states, i.e. organisms are difficult to isolate and serology tests are negative or indeterminate.

Immunological Binding Assays

The presence of particular microorganisms can be detected using several well recognized specific binding assays based on immunological results. (See for example, U.S. Pat. Nos. 4,366,241; 4,376,110; 4,517,288; and 4,837,168, which are hereby incorporated by reference.) For a review of the general procedures of the invention, see also *Basic and Clinical Immunology* 7th Edition (D. Stites and A. Terr ed.) 1991, which is hereby incorporated by reference.

The assays of the invention can be either competitive or noncompetitive. In competitive binding assays, the sample analyte (in this case, target antibodies to the microorganism associated with STD) competes with a labeled analyte for specific binding sites on a capture agent (e.g., antigens derived from the target microorganism) bound to a solid surface. The concentration of labeled analyte bound to the capture agent is inversely proportional to the amount of free analyte present in the sample.

Noncompetitive assays are typically sandwich assays, in which the sample analyte (target antibody) is bound between two analyte-specific binding reagents. One of the binding agents is used as a capture agent and is bound to a solid surface. The other binding agent is labelled and is used to measure or detect the resultant complex by visual or instrument means.

A number of combinations of capture agent and labelled binding agent can be used. For instance, antigens derived from the target microorganism can be used as the capture agent and labelled anti-human antibodies specific for the constant region of human antibodies can be used as the labelled binding agent. Goat, sheep and other non-human antibodies specific for human immunoglobulin constant regions γ or μ) are well known in the art. Alternatively, the anti-human antibodies can be the capture agent and the antigen can be labelled.

Other proteins capable of specifically binding human immunoglobulin constant regions, such as protein A or protein G may also be used as the capture agent or labelled binding agent. These proteins are normal constituents of the cell walls of streptococcal bacteria. They exhibit a strong nonimmunogenic reactivity with immunoglobulin constant regions from a variety of species. See, generally Kronval, et al., *J. Immunol.*, 111:1401-1406 (1973), and Akerstrom, et al., *J. Immunol.*, 135:2589-2542 (1985).

The non-competitive assays need not be sandwich assays. For instance, the antibodies in the sample can be bound directly to the solid surface. The presence of antibodies to the target microorganism in the sample can then be detected using labelled antigen.

Western blot (immunoblot) analysis can also be used to detect the presence of antibodies to the target microorganism in the sample. This technique is a reliable method for confirming the presence of target antibodies in the sample. The technique generally comprises separating proteins by gel electrophoresis on the basis of molecular weight, transferring the separated proteins to a suitable solid support, (such as a nitrocellulose filter, a nylon filter, or derivatized nylon filter), and incubating the sample with the separated proteins. This causes specific target antibodies present in the sample to bind their respective proteins. Target antibodies are then detected using labeled anti-human antibodies. This method of detecting target antibodies has the additional advantage of detecting antibodies to specific antigenic proteins.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34-41 (1986), which is incorporated herein by reference).

Some assay formats do not require the use of labelled components. For instance, agglutination assays can be used to detect the presence of the target antibodies. In this case, antigen-coated particles are agglutinated by samples comprising the target antibodies. In this format, none of the components need be labelled and the presence of the target antibody is detected by simple visual inspection.

As mentioned above, depending upon the assay, various components, including the antigen, target antibody, or anti-human antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC or polystyrene) or a bead. The desired component may be covalently bound or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See for example Immobilized Enzymes, Ichiro Chibata, Halsted Press, New York, 1978, and Cuatrecasas, *J. Biol. Chem.* 245 3059 (1970) which is incorporated herein by reference.

In addition to covalent bonding, various methods for noncovalently binding an assay component can be used. Noncovalent binding is typically nonspecific absorption of a compound to the surface. Typically, the surface is blocked with a second compound to prevent nonspecific binding of labelled assay components. Alternatively, the surface is designed such that it nonspecifically binds one component but does not significantly bind another. For example, a surface bearing a lectin such as Concanavalin A will bind a carbohydrate containing compound but not a labelled protein that lacks glycosylation. Various solid surfaces for use in noncovalent attachment of assay components are reviewed in U.S. Pat. Nos. 4,447,576 and 4,254,082, which are incorporated herein by reference.

Many assay formats employ labelled assay components. The labelling systems of the invention can be in a variety of forms. The label may be coupled directly or indirectly to the desired component of the assay according to methods well known in the art. A wide variety of labels may be used. The component may be labelled by any one of several methods. The most common method of detection is the use of autoradiography with $^{13}$H, $^{125}$I, $^{35}$S, $^{14}$C, or $^{32}$P labelled compounds or the like. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

Non-radioactive labels are often attached by indirect means. Generally, a ligand molecule (e.g., biotin) is covalently bound to the molecule. The ligand then binds to fan anti-ligand (e.g., streptavidin) molecule which is either inherently detectable or covalently bound to a signal system, such as a detectable enzyme, a fluorescent compound, or a chemiluminescent compound. A number of ligands and antiligands can be used. Where a ligand has a natural antiligand, for example, biotin, thyroxine, and cortisol, it can be used in conjunction with the labelled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see, U.S. Pat. No. 4,391,904, which is incorporated herein by reference.

In the present invention, the antigen used in the assay can be whole cells or proteins isolated from the target microorganism, or recombinantly produced proteins. For instance, in the case of C. trachomatis, the major outer membrane protein (MOMP) is conveniently used. This protein is a 39.5 kDa membrane glycoprotein responsible for the majority of serologic reactions among the various C. trachomatis serovars. Isolation and characterization of this glycoprotein is disclosed in U.S. Pat. No. 4,427,782, which is incorporated herein by reference.

If desired, synthetic or recombinant polypeptides comprising the immunogenic determinants from an antigenic protein can be used as the antigens. The polypeptides may be glycosylated as they occur in nature, or the glycosylation may be modified as a result of recombinant expression in other systems or by other means well known to one of skill in the art. Identification of sequences specifically recognized by lymphocytes can be determined in a number of ways. For instance, immune specificity can be determined by measuring the ability of overlapping peptides from the protein to induce proliferation of antigen-specific T cells. Such a technique has been used to identify determinants in MOMP from C. trachomatis (Ishikazi et al., Infect. and Immun. 60:3714-3718 (1992), which is incorporated herein by reference).

The biological sample used in the assays of the invention is any non-blood biological fluid containing antibodies, e.g., urine, saliva, cerebrospinal fluid, semen, and the like. The biological sample is preferably urine. The sample is typically taken from a human patient, but the assays can be used to detect antibodies in samples from any mammal, such as dogs, cats, sheep, cattle, and pigs.

The sample may be pretreated as necessary by dilution in an appropriate buffer solution or concentration if desired. Any of a number of standard aqueous buffer solutions, employing one of a variety of buffers, such as phosphate, Tris, or the like, at physiological pH can be used.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 15° to 40° C.

In another aspect, the present invention can be provided in a kit format for detecting target antibodies to microorganisms associated with STDs. Such a kit includes antigens specifically recognized by the target antibodies and a labelling system, including enzyme substrates and the like, suitable for detecting the immune complexes formed by the antigens and target antibodies. The kits also include appropriate washing solutions, dilution buffers and the like for preparation and analysis of urine samples.

The following examples are provided by way of illustration, not limitation.

EXAMPLES

Example I:

This example demonstrates that assays of the invention can detect antibodies to Chlamydia in urine of high risk individuals using Western blot analysis.

A. Materials and Methods for preparation of C. trachomatis immunoblots.
1) Preparative gels (polyacrylamide-SDS slab gels; Bio-Rad Mini-Protean II Dual Slab Cell system) each consisting of a 12% T resolving gel and a 4% T stacking gel were prepared according to standard procedures.
2) C. trachomatis LGV2 Strain 434 containing $10^{10}$ elementary bodies/ml [Biodesign, Inc. catalog number R12101 lot 4991 (May 8, 1992) and lot 191 (Oct. 29, 1992) were diluted to 0.75 mg/ml (both lots) with 2X Chlamydia Sample Buffer [20% glycerol; 2.5% SDS; 0.1 M Tris-HCl; 5% 2-mercaptoethanol; 0.005% bromophenol blue; and heated at 100° C. for 10 minutes.
3) Prestained Protein Molecular Weight Standards 14.3K–200K MW (Gibco BRL catalog number 6041LA; mixture of 7 proteins) was diluted to 3.5 mg/ml (0.5 mg/ml each protein) with 2X Chlamydia Sample Buffer (formula cited above in A.2) and heated at 100° C. for 5 minutes.
4) The preparative gels were each loaded with 100 μg denatured C. trachomatis (preparative lane) and 17.5 μg denatured Gibco BRL standard (reference lane). These samples were electrophoresed in a discontinuous buffer system [0.025 M Tris; 0.192 M glycine; 0.1% SDS, pH 8.4].
5) Following polyacrylamide gel electrophoresis (PAGE), the reference lane portion and approximately 2 mm of the preparative lane portion of each preparative gel were separately stained with 0.3% Coomassie brilliant blue R250 (placed on rocking platform for 2 hours, room temperature) and then destained with destainer containing 22.5% isopropyl alcohol and 10% glacial acetic acid.

6) Following PAGE, the remaining preparative lane portions of the preparative gels (after A.5) were equilibrated separately in iX blot buffer [0.025 M Tris; 0.192 M glycine; 20% methanol, pH 8.3] for approximately 20 minutes, then transferred for 80–90 minutes (112 volts, 0.4 amperes) to Immobilon-PVDF transfer membranes, pore size 0.45 μm (Millipore catalog number IPVH304FO).

7) Following electrophoretic transfer, each transfer membrane was cut into 2 mm strips [yielding 20–25 immunoblots (approx. 4–5 μg $C$. $trachomatis$ protein per immunoblot)] and blocked separately with 3% each of bovine, equine and goat serum in TBS containing 0.1% sodium azide (placed on a rocking platform for 1.5 hours, room temperature). $C.$ $trachomatis$ blots were then stored at 2–8 degrees C. in TBS containing 0.1% sodium azide (each set of blots derived from a single transfer membrane). Following electrophoretic transfer each preparative lane (gel) was stained and destained according to instructions in A.5.

B. Western blot procedures were performed on $C.$ $trachomatis$ immunoblots as briefly outlined below:

1) A purified $IgG_1$ monoclonal antibody to MOMP [Biodesign International catalog number C65651M (100 μg/ml)] was used to identify the location of the 39.5K MW MOMP on $C.$ $trachoreatis$ immunoblots.

2) Monoclonal antibody to MOMP must be run as necessary with each set of immunoblots (each set of immunoblots derives from a single transfer membrane).

3) $C.$ $trachomatis$ immunoblots were placed in alternate troughs on a rocking platform at room temperature.

4) $C.$ $trachomatis$ immunoblots were washed (followed by aspiration) with 1 ml TBS/Tween (50 mMTris; 200 mMNaCl; 0.3% Tween-20, pH 7.2+/−0.2) for at least 2 minutes 4 times.

5) 0.25 ml Western Blot (WB) Sample Diluent (3% each of bovine, equine and goat serum plus 0.01% each of bovine IgG coated beads, equine IgG coated beads and goat IgG coated beads plus 0.1% NP-40 in TBS containing 0.1% sodium azide) was prepared for dilution of samples.

6) The selected urine sample populations are outlined below:
  a. HIV-1 negative urine pool: 0215-17-1
  b. ARC/AIDS; HIV-1 positive populations: U-04308; 04311; U-04236; U-04240
  c. Drug rehabilitation population: DR 1-21.
  d. Insurance applicant population: IA 1-20

7) A serum sample derived from an individual previously infected with $C.$ $trachomatis$ was included with the urine $C.$ $trachomatis$ Western blot screen.

8) Sample incubation procedure:
  a. 3 sets of $C.$ $trachomatis$ immunoblots were utilized: 4991-3; 191-1; 191-2 [each set derives from gels loaded with C. trachomatis at 100 μg/gel (approximately 4–5 μg/immunoblot)].
  b. Reagent blanks were included with each of the 3 sets of $C.$ $trachomatis$ immunoblots (0.5 ml WB Sample Diluent per trough). Note that goat anti-human (GAH) conjugate (see B.10a) was utilized in connection with these reagent blanks.
  c. Human positive serum was diluted 1/100 with WB Sample Diluent in a polypropylene tube and transferred to troughs as applicable (0.5 ml per trough). Note that 1/100 human positive serum was included with each of the 3 sets of $C.$ $trachomatis$ immunoblots.
  d. Normal mouse serum was diluted 1/200 with WB Sample Diluent in a polypropylene tube and transferred to troughs as applicable (0.5 ml per trough). Note that 1/200 normal mouse serum was included with each of the 3 sets of $C.$ $trachomatis$ immunoblots.
  e. Monoclonal antibody to $C.$ $trachomatis$ MOMP was diluted 1/5 (20 μg/ml) with WB Sample Diluent in a polypropylene tube and transferred to troughs as applicable (0.5 ml per trough). Note that 20 μg/ml MOMP monoclonal was included with each of the 3 sets of $C.$ $trachomatis$ immunoblots.
  f. 0.25 ml of urine samples were added to troughs containing 0.25 ml WB Sample Diluent for a ½ dilution of each urine sample.
  g. Samples were incubated with $C.$ $trachomatis$ immunoblots overnight at room temperature on a rocking platform (15 hours).

9) Following sample incubation, samples were aspirated from the troughs and immunoblots were washed as stated in B.4.

10) Conjugate preparations:
  a. Alkaline phosphatase conjugated affinity purified goat anti-human (GAH) IgG/IgM (H+L) [Jackson Laboratories catalog number 109-055-1289] was diluted 1/2000 with 5% goat serum in TBS containing 0.1% sodium azide. 0.5 ml of 1/2000 GAH conjugate was added to each immunoblot previously incubated with a urine sample (see B.8f), human positive serum sample (see B.8c) or a reagent blank (see B.8b).
  b. Alkaline phosphatase conjugated affinity purified goat anti-mouse (GAM) IgG (H+L) [Jackson Laboratories catalog number 115-055-100] was diluted 1/2000 with 5% goat serum in TBS containing 0.1% sodium azide. 0.5 ml 1/2000 GAM conjugate was added to the immunoblots incubated with the MOMP monoclonal (see B.8e) or normal mouse serum (see B.8d).

11) Immunoblots were incubated with conjugate for 1 hour. Following incubation, conjugate was aspirated from the troughs.

(12) Immunoblots were washed two times as stated in B.4.

13) Immunoblots were washed two more times as stated in B.4 but using 1X Substrate Buffer for alkaline phosphatase [prepared by diluting 10X Substrate Buffer (Zymed catalog number 00-2208) to 1X with high purity water].

14) 0.5 ml of substrate solution [0.05 mg/ml BCIP plus 0.1% NBT in 1X Substrate Buffer for alkaline phosphatase (see B.13)] was added to each immunoblot.

15) Immunoblots were incubated with substrate solution for 10 minutes.

16) Substrate solution was aspirated and immunoblots were washed (followed by aspiration) with 1 ml high purity water for at least 2 minutes 4 times.

17) Immunoblot trays were covered and air-dried for a minimum of 1 hour before recording results.

C. Results of $C.$ $trachomatis$ PAGE and Protein Transfer.

1) The reference lane portions (and 2 mm preparative lane strips) of the preparative gels corresponding to $C.$ $trachomatis$ $lot$ 4991, following PAGE and gel processing, exhibited distinct bands running just below the 43K MW and 18.4K MW bands relative to the standard and indistinct multiple bands running above and below the 43K MW band relative to the standard. Comparison of the remaining preparative gels, following protein transfer and gel processing, to the reference lane portions (and 2 mm preparative lane strips) indicated protein transfer to the membranes was no greater than 50%.

2) The reference lane portions (and 2 mm preparative lane strips) of the preparative gels corresponding to *C. trachomatis* lot 191, following PAGE and gel processing, exhibited distinct bands running just below the 43K MW and 18.4K MW bands and at the dye front (14.3K MW band) relative to the standard. Indistinct multiple bands running above and below the 43K MW band relative to the standard were also observed. Comparison of the remaining preparative gels, following protein transfer and gel processing, to the reference lane portions (and 2 mm preparative lane strips) indicated protein transfer to the membranes was no greater than 50%.

D. *C. trachomatis* Western blot results for screen of selected urines

Sample immunoblots from the drug rehabilitation population are shown in FIG. 1. Results of the immunoblots for all populations are presented in Table 1. EIA O.D. values (Example 2) are included for easy reference in Table 1. In Table 1, a negative test result indicates an absence of any bands or background on a dry *C. trachomatis* immunoblot. A positive test result indicates reactivity to MOMP on a dry *C. trachomatis* immunoblot (compared to immunoblot incubated with MOMP monoclonal). An indeterminate test result indicates any pattern of one or more bands on a dry *C. trachomatis* immunoblot that does not meet the positive criterion and/or background along a dry *C. trachomatis* immunoblot.

E. Summary of Results in Table 1:

a. 0215-17-1 (HIV-1 negative urine pool) yielded a negative result.

b. ¾ urine samples derived from ARC/AIDS; HIV-1 positive subjects yielded positive results. One of the urine samples yielded an indeterminate result due to smearing in the MOMP region (U-04240).

c. 18/21 urine samples derived from a drug rehabilitation population yielded a positive result.

d. 11/20 urine samples derived from an insurance applicant population yielded a positive result.

TABLE 1

| Sample | MOMP Test Result | Other Bands | EIA O.D. |
|---|---|---|---|
| Normal mouse serum 1/200 | indeterminate | 1 below MOMP region | N/A |
| MOMP MAb 20 μg/ml | positive | none | N/A |
| Reagents/GAH | negative | none | 0.090 |
| Positive human serum 1/100 | positive | 5 > MOMP (1 just below 68K area) | 1.880 |
| 0215-17-1 | negative | none | 0.083 |
| U-04236 | positive | 2 above MOMP | 0.419 |
| U-04240 | indeterminate | none | 0.284 |
| U-04308 | positive | none | 0.323 |
| U-04311 | positive | none | 0.198 |
| DR-7 | positive | 4 above MOMP 4 below MOMP | 0.878 |

TABLE 1-continued

| Sample | MOMP Test Result | Other Bands | EIA O.D. |
|---|---|---|---|
| DR-14 | indeterminate | 1 above MOMP region | 0.323 |
| Set 2: | | | |
| Normal mouse serum 1/200 | negative | none | N/A |
| MOMP MAb 20 μg/ml | positive | none | N/A |
| Reagents/GAH | negative | none | 0.090 |
| Positive human serum 1/100 | positive | 5 > MOMP (1 just below 68K area); 3 below MOMP | 1.880 |
| DR-1 | positive | 7 above MOMP 8 below MOMP | >2.99 |
| DR-16 | negative | none | 0.207 |
| DR-13 | positive | 2 above MOMP 1 below MOMP | 0.387 |
| DR-17 | positive | none | 0.186 |
| DR-2 | positive | 1 above MOMP 2 below MOMP | 1.811 |
| DR-9 | positive | 5 above MOMP | 0.560 |
| DR-12 | positive | 3 above MOMP | 0.442 |
| DR-19 | positive | none | 0.132 |
| DR-3 | positive | 6 above MOMP 6 below MOMP | 1.682 |
| DR-10 | positive | 4 above MOMP 1 below MOMP | 0.526 |
| DR-4 | positive | 5 above MOMP 4 below MOMP | 1.281 |
| DR-5 | positive | 2 above MOMP 3 below MOMP | 0.980 |
| DR-15 | positive | 4 > MOMP (1 just below 68K area) | 0.318 |
| DR-21 | negative | none | 0.105 |
| DR-6 | positive | 3 above MOMP | 0.929 |
| DR-8 | positive | 4 above MOMP 1 below MOMP | 0.633 |
| DR-11 | positive | 1 below MOMP | 0.498 |
| DR-20 | positive | none | 0.106 |
| DR-18 | positive | none | 0.153 |
| Set 3: | | | |
| Normal mouse serum 1/200 | negative | none | N/A |
| MOMP MAb 20 μg/ml | positive | none | N/A |
| Reagents/GAH | negative | none | 0.090 |
| Positive human serum 1/100 | positive | 5 > MOMP (1 just below 68K area) | 1.880 |
| IA-1 | positive | 3 above MOMP 1 below MOMP | 1.031 |
| IA-13 | negative | none | 0.135 |
| IA-15 | negative | none | 0.093 |
| IA-8 | positive | 3 above MOMP 2 below MOMP | 0.356 |
| IA-6 | positive | 3 above MOMP 2 below MOMP | 0.414 |
| IA-14 | indeterminate | 1 below MOMP region | 0.130 |
| IA-20 | negative | none | 0.077 |
| IA-16 | negative | none | 0.093 |
| IA-18 | negative | none | 0.090 |
| IA-9 | positive | 2 > MOMP (1 just below 68K area) | 0.314 |
| IA-3 | positive | none | 0.763 |
| IA-7 | positive | 1 above MOMP 1 below MOMP | 0.379 |
| IA-12 | negative | none | 0.200 |
| IA-19 | negative | none | 0.079 |
| IA-4 | positive | 2 above MOMP | 0.499 |
| IA-11 | positive | none | 0.243 |
| IA-17 | negative | none | 0.092 |
| IA-10 | positive | none | 0.289 |
| IA-5 | positive | none | 0.438 |
| IA-2 | positive | 6 above MOMP | 0.832 |

TABLE 1-continued

| Sample | MOMP Test Result | Other Bands | EIA O.D. |
|---|---|---|---|
| | | 5 below MOMP | |

EXAMPLE 2

This example shows the ability of enzyme immunoassays (EIA) of the invention to detect antibodies to C. trachomatis in human urine.

MATERIALS AND METHODS

1). C. trachomatis LGV2 Strain 434 containing $10^{10}$ elementary bodies/ml (Biodesign, Inc. catalog number R12101 lot 191) was diluted to 0.75 mg/ml with Chlamydia Buffer (1% SDS; 0.1 M Tris-HCl; 2.5% 2-mercaptoethanol) and heated at 100° C. for 10 minutes. Final Chlamydia Buffer concentration: 0.5% SDS; 0.05 M Tris-HC1; 1.25% 2-mercaptoethanol.

2) C. trachomatis coated strips were prepared as follows:
  a. 8 Immulon 2 Dividastrips 2×8 (Dynatech catalog number 011-010-6202) were secured into a microplate frame (Dynatech 011-010-6603).
  b. Treated C. trachomatis (see 1, above) was diluted to 10 µg/ml with sodium bicarbonate buffer, pH 9.6. Final Chlamydia Buffer concentration: 0.007% SDS; 0.67 mMTris-HCL; 0.017% 2-mercaptoethanol.
  c. 100 µl per well of the 10 µg/ml solution was added to strip wells for 1 µg per well treated C. trachomatis. The coated strips were incubated overnight at room temperature (20°–25° C.; 16–18 hours).
  d. Coated strips were then blocked with 5% goat serum (in TBS containing 0.1% sodium azide) for 1 hour at room temperature(20°–25° C.). Note that antigen solution was not aspirated prior to addition of the 5% goat serum block.
  e. The microplate frame was turned over to remove block and antigen solutions, then strip wells were blotted dry using paper towels.

3). The selected urine sample populations are outlined below:
  a. HIV-1 negative urine pool: 0215-17-1
  b. ARC/AIDS; HIV-1 positive populations: U-04308; U-04311; U-04236; U-04240
  c. Drug rehabilitation population: DR 1-21.
  d. Insurance applicant population: IA 1-20.

4). A serum sample derived from an individual previously infected with C. trachomatis was included with the urine C. trachomatis EIA screen.

5 ). C. trachomatis EIA:
  a. Sample incubation procedure:
    1. The positive serum sample was diluted 1/200 with 1/10 EIA Sample Buffer (3% each of bovine, equine and goat serum plus 0.001% each of bovine IgG coated beads, equine IgG coated beads and goat IgG coated beads in TBS containing 0.1% sodium azide) in a polypropylene tube. The diluted serum sample was pre-incubated 5 minutes at room temperature (20°–25° C.) and then transferred to 2 wells at 200 µl per well.
    2. 25 µl EIA Sample Buffer (30% each of bovine, equine and goat serum plus 0.01% each of bovine IgG coated beads, equine IgG coated beads and goat IgG coated beads in TBS containing 0.1% sodium azide) was added to each well designated for test urine samples and to 2 wells designated for the reagent blank.
    3. 200 µl TBS containing 0.1% sodium azide was added to each of the 2 wells designated as the reagent blank.
    4. 200 µl of each urine sample was added to replicate wells containing EIA Sample Buffer.
    5. The wells were incubated with samples for 2 hours at 37° C.
  b. The wells were washed 6 times with Wash Solution (TBS containing 0.1% sodium azide plus 0.1% NP-40) using an automated microplate washer (Bio-Tek® Model EL403H).
  c. Alkaline phosphatase conjugated affinity purified goat anti-human (GAH) IgG/IgM (H+L) [Jackson Laboratories catalog number 109-055-1289] was diluted 1/2000 with 5% goat serum (in TBS containing 0.1% sodium azide).
  d. 1/2000 GAH conjugate was added to each well at 100 µl per well. The wells were incubated with conjugate for 1 hour at 37° C.
  e. The wells were washed as stated in 5b.
  f. 1 mg/ml p-nitrophenyl phosphate (PNPP) substrate was prepared using 5 mg PNPP tablets (Sigma catalog number N-9389) and Substrate Diluent [10% diethanolamine (DEA) in high purity water containing 0.1% sodium azide].
  g. 100 µl substrate was added to each well. The wells were incubated with substrate at 37° C. for no longer than 60 minutes.
  h. After 60 minutes, 50 µl Stop Solution [400 mM ethylenediaminetetraacetic acid (EDTA)] was added to each well.
  i. The microplate was read using a Bio-Tek EL312E Kinetic Reader at a dual wavelength setting of 405 nm (test wavelength)/630 nm (reference wavelength) and no shaking.

Figure 2:
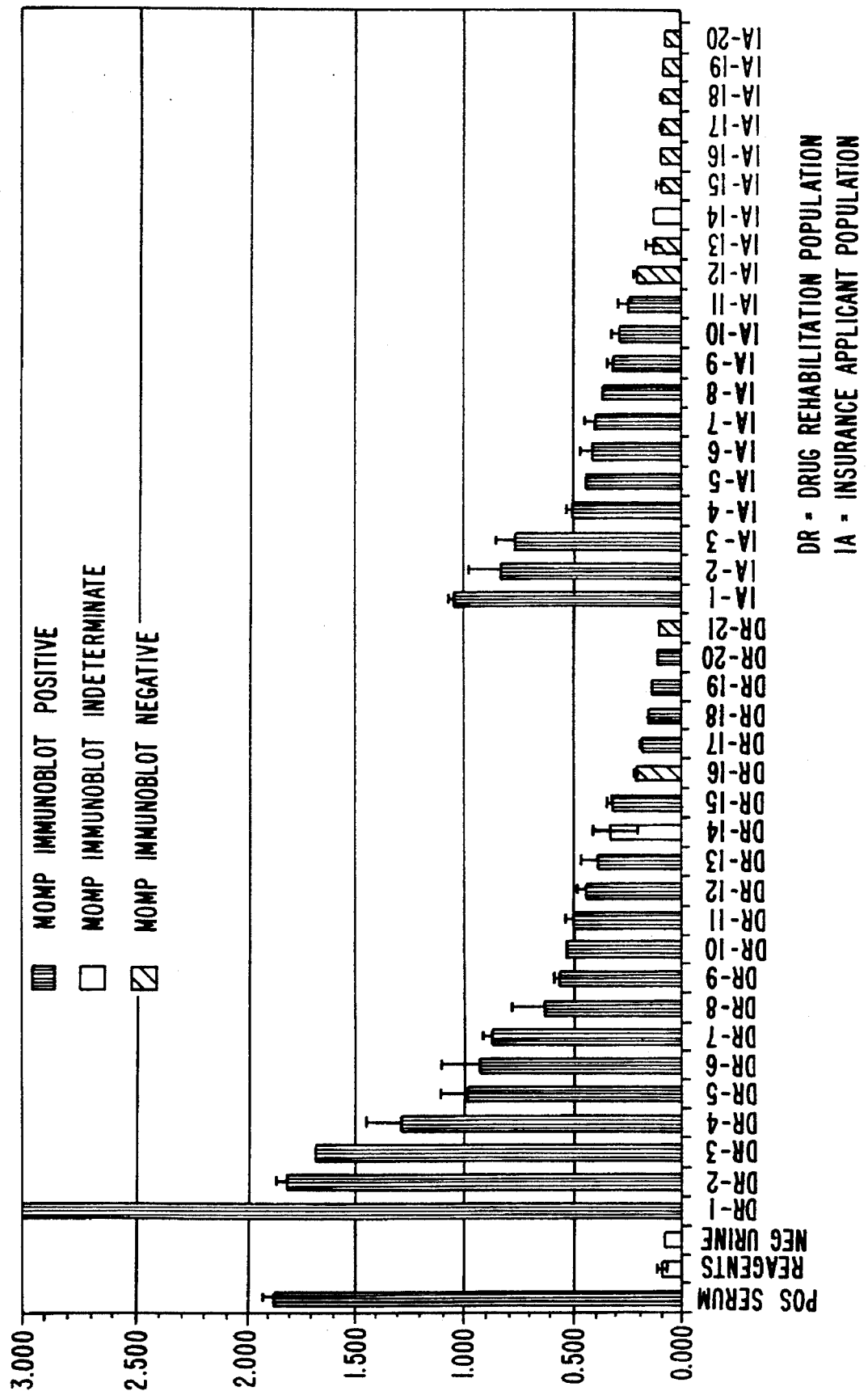
FIG. 2 shows the results of *C. trachomatis* urine antibody enzyme immunoassays (EIA).

The results of the EIA are presented in FIG. 2. C. trachomatis immunoblot results (Example 1) are presented for each sample, as well.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A method for detecting the presence of an antibody which specifically binds to *Chlamidia trachomatis* in a urine sample, the method comprising:
    contacting the urine sample with an antigen from said *Chlamydia trachomatis*; and detecting the formation of an antigen-antibody complex.

2. The method of claim 1, wherein the antigen is a chlamydial surface protein.

3. The method of claim 2, wherein the surface protein is major outer membrane protein.

4. The method of claim 1, wherein the urine is human urine.

5. The method of claim 1, wherein the antigen is bound to a solid surface.

6. The method of claim 5, wherein the antigen is noncovalently bound to the solid surface.

7. The method of claim 5, wherein the solid surface is a well of a microtiter plate.

8. The method of claims 5, wherein the solid surface is nitrocellulose, or polyvinylidene difluoride.

9. The method of claim 1, wherein the antigen-antibody complex is detected using a labeled anti-human antibody.

10. The method of claim 9, wherein the label is a radiolabel.

11. The method of claim 9, wherein the label is a detectable enzyme.

12. The method of claim 11, wherein the detectable enzyme is alkaline phosphatase.

13. The method of claim 1, further comprising the step of binding the antibody or antigen-antibody complex to a solid surface.

14. The method of claim 13, wherein the antibody is bound to the solid surface through an anti-human antibody.

15. The method of claim 13, wherein the antigen is labeled and the antigen-antibody complex is detected by measuring the label on the solid surface.

16. The method of claim 15, wherein the label is a radiolabel.

17. The method of claim 15, wherein the label is a detectable enzyme.

18. The method of claim 17, wherein the detectable enzyme is alkaline phosphatase.

19. The method of claim 13, wherein the solid surface is a well of a microtiter plate.

20. The method of claim 1, wherein the antigen-antibody complex is detected by agglutination of the complex.

* * * * *